Figure 1:
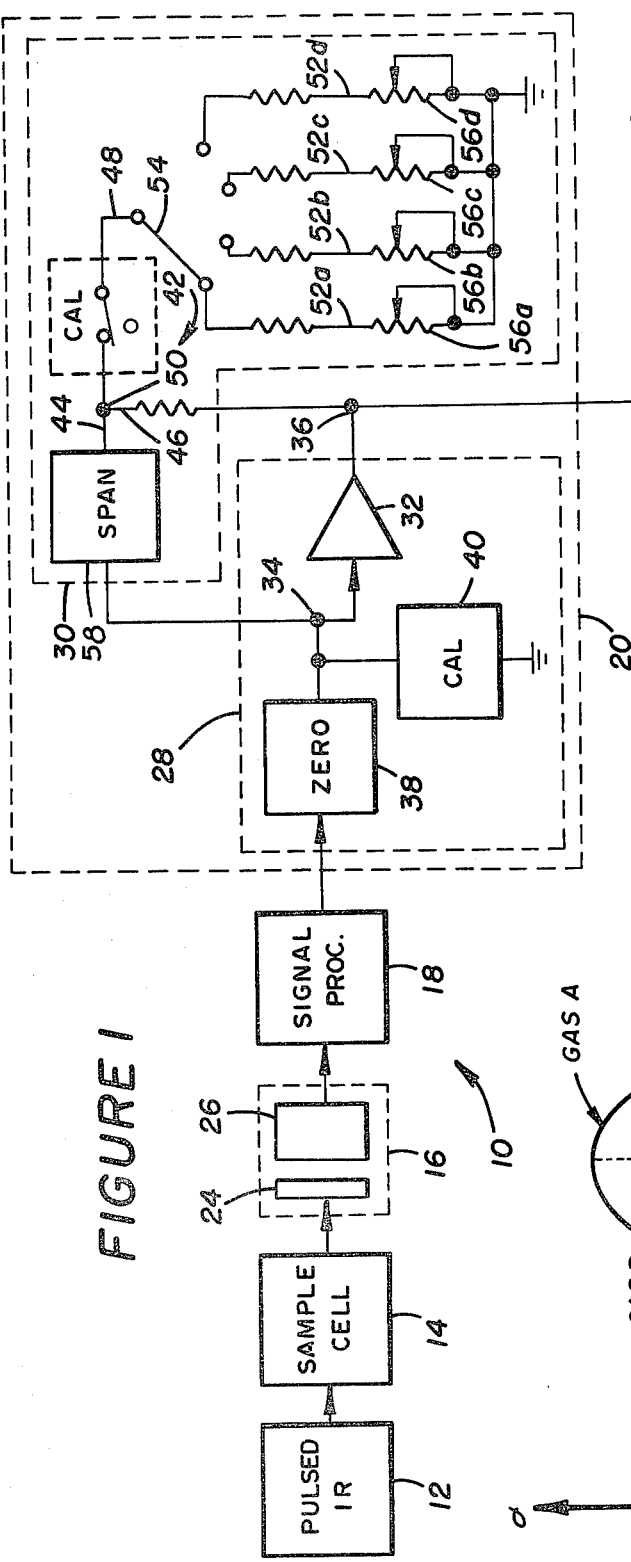

United States Patent [19]

Burough et al.

[11] Patent Number: 4,480,190
[45] Date of Patent: Oct. 30, 1984

[54] NON-DISPERSIVE INFRARED GAS ANALYZER

[75] Inventors: Irvin G. Burough, Walnut Creek; Kevin G. Williams, Pinole, both of Calif.

[73] Assignee: Andros Analyzers Incorporated, Berkeley, Calif.

[21] Appl. No.: 380,449

[22] Filed: May 20, 1982

[51] Int. Cl.³ ............................................. G01N 21/17
[52] U.S. Cl. ..................................... 250/343; 356/437
[58] Field of Search ................ 250/373, 339, 343, 344, 250/345; 356/437

[56] References Cited

U.S. PATENT DOCUMENTS

| | | | |
|---|---|---|---|
| 3,004,664 | 10/1961 | Dreyfus | 250/343 |
| 3,887,473 | 6/1975 | Sternberg et al. | 250/345 |
| 3,953,734 | 4/1976 | Dimeff | 250/343 |
| 4,013,260 | 3/1977 | McClatchie et al. | 250/343 |
| 4,346,296 | 8/1982 | Passaro et al. | 250/343 |

Primary Examiner—Alfred E. Smith
Assistant Examiner—Carolyn E. Fields
Attorney, Agent, or Firm—Fitch, Even, Tabin & Flannery

[57] ABSTRACT

Pulse modulated infrared energy is directed through a sample cell containing a gas mixture. The gas mixture may include a selected one of a plurality of gases. Each gas exhibits a characteristic absorption in the infrared wavelengths. A detector responsive to infrared energy at a preselected wavelength develops an AC signal having an amplitude proportional to the infrared energy passing through the sample cell at the preselected wavelength and having a frequency corresponding to the preselected pulse modulation frequency. The preselected wavelength is common to the absorption characteristic of each of said gases. The AC signal is processed to develop a DC signal having an amplitude determined from the AC signal. The DC signal is applied to an amplifier having a variable gain feedback which provides a plurality of gain steps. Each gain step is associated with a different one of the gases a single surrogate gas may be used to calibrate each gain step. The DC signal is amplified by the appropriate gain step to develop a second DC signal proportional to the concentration of the gas and the mixture contained in the sample cell. The amplifier may further include an analog to digital convertor which stores a digital equivalent of a zero offset output voltage of the amplifier when its input is grounded. The digital signal is reconverted to an analog signal and a current proportional to such signal is normally applied to the input of the amplifier to maintain zero stability.

10 Claims, 3 Drawing Figures

NON-DISPERSIVE INFRARED GAS ANALYZER

The present invention relates generally to gas analyzers and, more particularly, to an improved non-dispersive infrared gas analyzer which accurately measures a concentration of a selected one of a plurality of gases which may be contained in a gas mixture.

Non-dispersive infrared gas analyzers typically utilize a source of infrared energy directed through an unknown gas mixture contained in a sample cell. The energy passing through the sample cell is detected and electrical signals are produced commensurately therewith. These signals are processed to produce an output indicating the concentration of one or more of the constituents of the mixture in the sample cell.

Such gas analyzers utilize the principle that various gases exhibit substantial absorption characteristics at specific wavelengths in the infrared radiation spectrum. A gas analyzer of this type is shown and described in U.S. Pat. No. 4,013,260, McClatchie et al, issued Mar. 22, 1977, and assigned to the assignee of the present invention. Another type of non-dispersive infrared gas analyzer is shown and described in U.S. Pat. No. 3,953,734, Dimeff, issued Apr. 27, 1976, and assigned to the United States of America.

In both of the above cited patents, and in similar types of infrared gas analyzers, the beam of infrared energy passing through the sample cell containing the unknown gas mixture is varied by the interposition of one or more filters such as on a filter wheel in the path of the infrared energy beam. Typically, each filter only passes radiation at the characteristic absorption wavelength of a particular gas of interest. Another filter may also be used as a reference filter at a wavelength close to but not overlapping the characteristic absorption wavelength of any of the gases present in the sample cell.

Such prior art devices typically require the generation of some type of synchronizing signal in order to coordinate the operation of the signal processing circuitry with the rotation of the filter wheel.

Instead of employing a rotary filter wheel, a more simple type of gas analyzer may utilize a stationary filter or filters with associated detectors and produce an AC signal on the detector by periodically interrupting the infrared energy beam, such as with a rotary chopper. A limitation and disadvantage of such devices is that each gas of interest has an associated filter matched to the characteristic wavelength of the gas.

Nevertheless, another limitation and disadvantage of chopper type gas analyzers is loss of zero stability in the signal processing circuitry over time to which the AC signal from the detector is applied, such signal processing circuitry developing a further signal commensurate with the concentration of the gas of interest in the mixture.

It is therefore an important object of the present invention to provide an improved non-dispersive infrared gas analyzer which overcomes one or more of the limitations and disadvantages enumerated hereinabove.

It is another object of the present invention to provide a non-dispersive infrared gas analyzer which measures the concentrations of a selected one of a plurality of gases of interest with the detector responsive to a preselected wavelength.

It is still a further object of the present invention to provide an improved infrared gas analyzer which automatically provides for zero stability in the signal processing circuitry.

Figure 2:
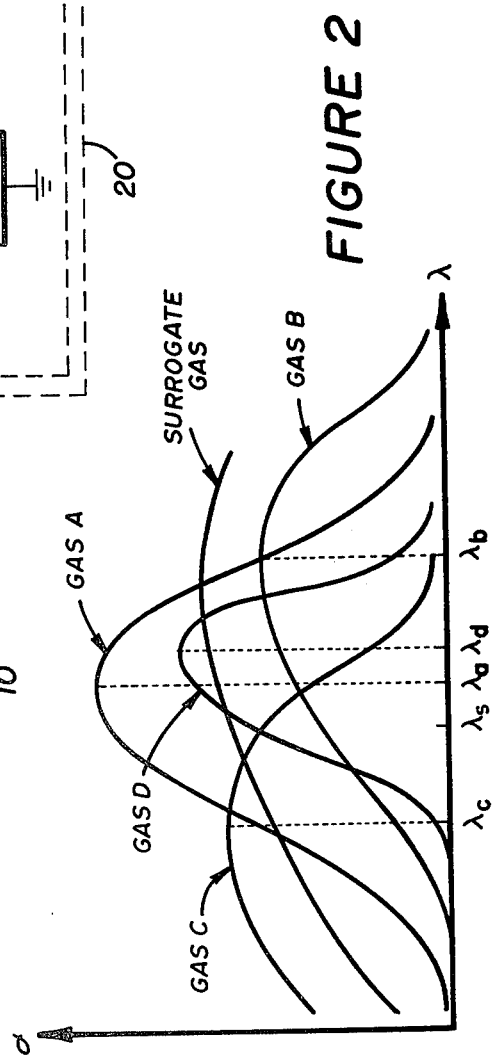
Figure 3:
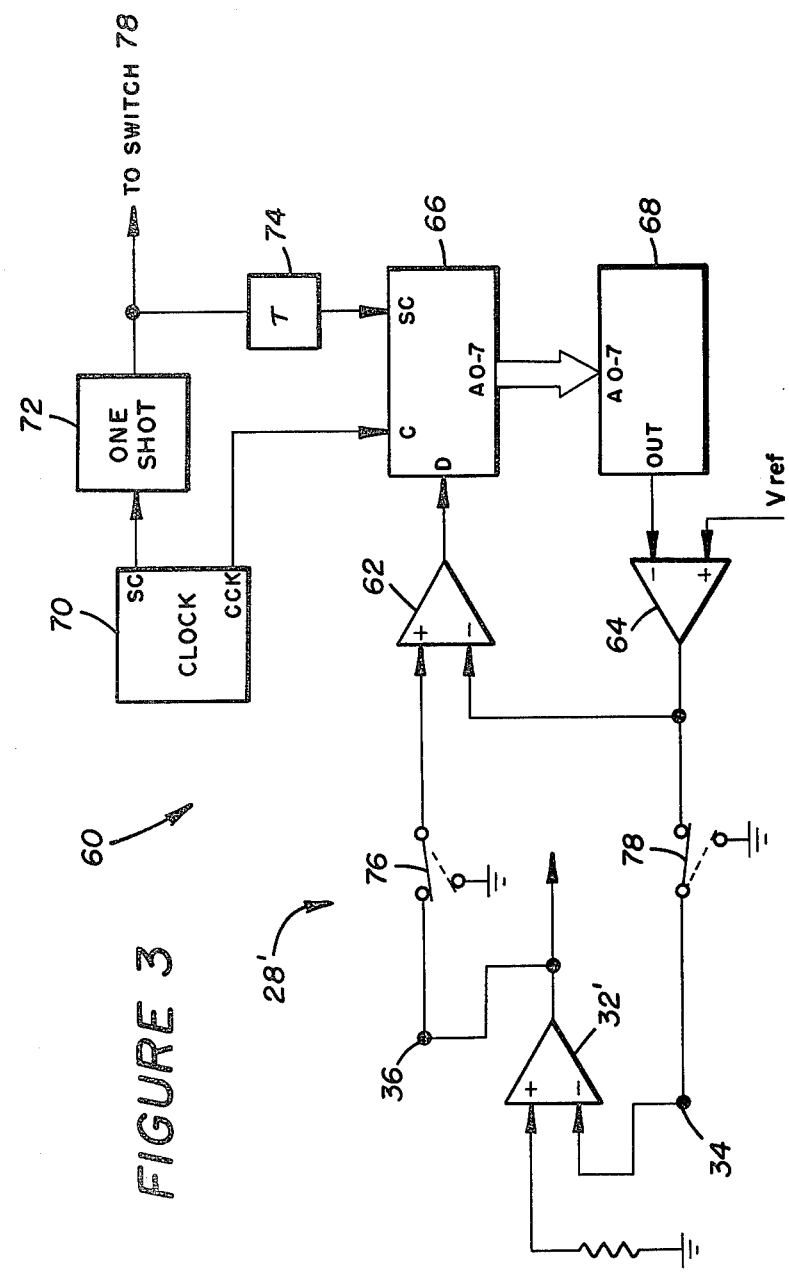

FIG. 1 is a schematic block diagram of one embodiment of a non-dispersive infrared gas analyzer according to the principles of the present invention; and FIG. 2 illustrates possible absorption characteristics for gases in an absorption vs. wavelength domain; and FIG. 3 is a schematic block diagram of a modification to a portion of the block diagram of FIG. 1.

Broadly stated, in one embodiment of the present invention, a pulse modulated source of infrared energy is directed through a sample cell containing a gas mixture to be analyzed. The gas mixture may include a selected one of a plurality of gases, each gas having an absorption characteristic. A detector is responsive to the infrared energy passing through the gas cell at a preselected wavelength and develops an AC signal having an amplitude determined by the infrared energy passing through the cell and a frequency corresponding to a preselected modulation frequency of the infrared energy. The AC signal is converted to a DC signal having an amplitude determined by the AC signal. The amplitude of the DC signal is then referenced commensurately with each of an absorption characteristic of the selected one of the gases in the mixture and the preselected wavelength of the detector. The reference DC signal is commensurate with the concentration of the selected one of the gases of interest.

Referring now to FIG. 1, there is shown a non-dispersive gas analyzer 10 including a pulse modulated source 12 of infrared energy, a sample cell 14, a detector means 16, a signal processing means 18, and a signal referencing means 20.

Source 12 emits pulse modulated infrared energy, the modulation being at a preselected frequency. In one embodiment of the present invention, source 12 may include means for directing infrared energy through cell 14 and means for periodically interrupting the infrared energy at the preselected frequency. Interrupting means may be a chopper wheel interposed the directing means and cell 14 or interposed cell 14 and detector means 16.

Cell 14 contains a gas mixture to be analyzed. The gas mixture includes a gas of interest being a selected one of a plurality of gases. Each of the gases has an absorption characteristic associated therewith, as hereinbelow described. As the infrared energy passes through cell 14, the gas mixture absorbs a portion of such energy.

Detector means 16 is responsive to the infrared energy passing through cell 14 at a preselected wavelength and develops an AC signal having an amplitude determined by the radiant energy passing through cell 14 at the preselected wavelength and a frequency corresponding to the preselected frequency of modulation of the infrared energy. The AC signal is applied to signal processing means 18. As hereafter described, the preselected wavelength is common to the absorption characteristic of each of the gases.

Signal processing means 18 develops a first DC signal in response to the AC signal applied thereto. The first DC signal has an amplitude determined from the AC signal and is applied to referencing means 20.

Referencing means 20 develops a second DC signal having an amplitude commensurate with a concentration of the gas of interest in the gas mixture contained in cell 14 in response to the first DC signal. The amplitude of the first DC signal is referenced commensurately with each of the absorption characteristic of the gas of interest and the preselected wavelength of infrared energy at which detector means 16 is responsive, such referencing determining the amplitude of the second DC signal.

Referring now to FIG. 2, there is shown, as an example only, an absorption ($\alpha$) versus wavelength ($\lambda$) representation 22 illustrating a possible absorption characteristic for four gases A, B, C and D. Each of gases A, B, C and D has a characteristic absorption wavelength $\lambda_a$, $\lambda_b$, $\lambda_c$ and $\lambda_d$, respectively. The absorption of infrared energy by the gas mixture is maximized when such energy is at the characteristic absorption wavelength $\lambda_{a-d}$ of the respective one of gases A–D. The characteristic absorption being all wavelengths at which a gas absorbs infrared energy. The preselected wavelength $\lambda_s$ is chosen to be common to each of the absorption characteristics of gases A–D as shown in FIG. 2.

Returning to FIG. 1, detector means 16 may include an optical filter 24 which passes infrared energy at the hereinabove described preselected wavelength $\lambda_s$ and a transducer 26 which converts the infrared energy to the hereinabove described AC signal.

Referencing means 20 includes an amplifier means 28 for developing the second DC signal in response to the first DC signal and a variable feedback means 30 for providing a plurality of gain steps in amplifier means 28. Each of the gain steps is associated with a different one of gases A–D.

Amplifier means 28 includes an amplifier 32 having an input 34 and an output 36, a zero set means 38 and a calibration means 40. Input 34 may hereinafter also be referred to as summing junction 34.

Variable feedback means 30 includes a T circuit 42 having a first conductive branch 44, a second conductive branch 46 and a third conductive branch 48, all coupled at a common node 50. First branch 44 is coupled between summing junction 34 and node 50. Second branch 46 is coupled between output 36 and node 50. Third branch 48 is coupled between node 50 and ground, and has a plurality of parallel conductive paths $52_{a-d}$ and a switch 54. Each of conductive paths $52_{a-d}$ is associated with a different one of the gain steps and hence associated with a difference one of gases A–D, respectively. Switch 54 selectively couples one of paths $52_{a-d}$ between node 50 and ground.

Each conductive path $52_{a-d}$ includes a variable resistance $56_{a-d}$, respectively. When a known concentration of one of gases A–D is present in cell 14, the respective one of resistances $56_{a-d}$ is set so that the amplitude of the second DC signal is commensurate with the known concentration.

First branch 44 of T circuit 42 includes a span set means 58 for adjusting the span on the second DC signal. Span set means 58 may include a variable, preset resistor serially coupled between summing junction 34 and node 50.

Zero set means 38 adjust the current at summing junction 34 to zero in the absence of any gas of interest in the gas mixture. Such an absence of the gas of interest may hereinafter be referred to as "zero air". Zero air does not contain any gas which absorbs infrared energy. Zero set means 38 may include a variable, preset resistor serially coupled between signal processing means 18 and summing junction 34.

Calibration means 40 calibrates amplifier 32 by applying a known current to summing junction 34, defining a calibration mode. Calibration means 40 may include a source of potential resistively coupled to summing junction 34, a variable calibration resistor resistively coupled to each of summing junction 34 and the potential source at a first end and to ground at a second end, and a normally closed calibration switch arranged for normally shorting the calibration resistor to ground at the first end thereof, defining a normal operating mode. The calibration switch opens during the calibration mode so that a current develops in the calibration resistor. The calibration resistor is adjusted while cell 14 contains a zero air gas mixture, thus calibrating the current at summing junction 34. Furthermore, the calibration switch normally couples third branch 48 of T circuit 42 to node 50 during the normal operating mode, and opens during the calibration mode to decouple third branch 48 from node 50.

Although not intended as a limitation of the present invention, infrared source 12, sample cell 14, detector means 16 and signal conditioning means 18 may be of a type as disclosed in commonly owned application Ser. No. 178,302 filed Aug. 15, 1980 and now U.S. Pat. No. 4,346,296, issued Aug. 24, 1982. The transfer function of amplifier 32 as a function of the resistances of zero set means 38, calibration means 40 and span set means 58 may be obtained from the hereinabove mentioned commonly owned application.

Gas analyzer 10 in one embodiment of the present invention is particularly useful as an anesthetic agent analyzer. A sample of the gas mixture having an anesthetic agent being given to a patient flows through sample cell 14. Typically, the anesthetic agent is one of halothane, penthrane, forane and ethrane, such agents normally having a 0–5% concentration in the gas mixture. Each of these anesthetic agents absorbs infrared energy at a wavelength of 3.3 microns. Thus, the preselected wavelength $\lambda_s$ of detector means 16, may in this embodiment, be 3.3 microns. However, at $\lambda_s$, each of these agents will absorb a different amount of infrared energy given an equal concentration of each agent in different gas mixtures, where each mixture contains only one of the agents. Thus, variable feedback means 30, and more particularly, each resistor $56_{a-d}$, is adjusted so that the first DC signal developed is amplified by a gain step so that the second DC signal has the same amplitude for equal concentrations of each agent in their respective gas mixture, provided that switch 54 is positioned to one of resistors $56_{a-d}$ associated with the agent in the gas mixture being analyzed.

In as much as the anesthetic agents are highly volatile, each resistor $56_{a-d}$ may be calibrated by introducing a surrogate gas into sample cell 14. The surrogate gas has an absorption characteristic overlapping the absorption characteristic of each of gases A–D, best seen in FIG. 2. The surrogate gas is further chosen to be easily and safely handled and may, in one embodiment of the present invention be methane. A relationship is predetermined between the characteristic absorption of each of gases A–D at the preselected wavelength and the characteristic absorption of the surrogate gas also at the preselected wavelength. When a known concentration of the surrogate gas is contained in sample cell 14, each of resistors $56_{a-d}$ is adjusted so that the second DC signal has amplitude which is determined from the predetermined relationship. When one of gases A–D is then introduced into cell 14, the second DC signal will be commensurate with the concentration of such one of gases A–D.

Referring now to FIG. 3, there is shown another embodiment 28' of amplifier means 28 of FIG. 1, which may hereinafter be referred to as amplifier means 28'. Amplifier means 28' as hereinafter described is an improvement in zero stable amplifiers.

Amplifier means 28' includes an amplifier 32' having a non-inverting input resistively coupled to ground, and summing junction 34 defined at the inverting input of amplifier 32'. Amplifier means 28' further includes an analog to digital converter means 60 for storing a digital reference signal and applying an analog reference current determined from the stored digital reference signal to summing junction 34. The digital reference signal is determined from the difference between the analog reference signal and the second DC signal developed when summing junction 34 is grounded.

Analog to digital converter means 60 includes a first comparator 62 having a non-inverting input, an inverting input and an output, a second comparator 64 having a non-inverting input, an inverting input and an output, a counter 66 having an analog data input D, a clock input C, a start count input SC and a digital output $A_{0-7}$, a digital to analog (D/A) converter 68 having a digital input $A_{0-7}$ and an analog output OUT, a clock 70 developing a fast clock signal at a first output CCK and a slow clock signal at a second output SC, a one shot multi-vibrator 72 having a trigger input T and an output Q, a time delay 74, a first switch 76 and a second switch 78. The non-inverting input of first comparator 62 is selectively coupled to one of output 36 of amplifier 32' or to ground by first switch 76. Summing junction 34 is selectively coupled to the inverting input of first comparator 62 or to ground by second switch 78. The non-inverting input of second comparator 64 is coupled to a source $V_{ref}$ of a reference potential. The inverting input of second comparator 64 is coupled to the output OUT of D/A convertor 68.

The data input D of counter 66 is coupled to the output of first comparator 62. The clock input C and start count input SC of counter 66 are coupled to the output CCK of clock 70 and output Q of one shot vibrator 72 through time delay 74, respectively. The digital input $A_{0-7}$ of D/A convertor 68 is coupled to the digital output $A_{0-7}$ of counter 66. The trigger T input of one shot vibrator 72 is coupled to the slow clock output SC of clock 70.

The slow clock signal developed by clock 70 has a relatively long time period between pulses of short duration. Each pulse initiates a zero calibration cycle. When the pulse of the slow clock signal is applied to the trigger input T of one shot multi-vibrator 72, multi-vibrator 72 develops a second pulse which is applied to second switch 78 to momentarily couple summing junction 34 to ground. This second pulse is momentarily delayed by time delay 74 defining a delayed pulse which is applied to start count input SC of counter 66. The second DC signal developed by amplifier 32' at output 36 while summing junction 34 is coupled to ground by switch 78 is a zero offset output voltage. First comparator 62 develops an analog difference signal proportional to the difference between zero offset output voltage and the signal developed by second comparator 64. The analog difference signal is clocked into counter 66 and digitized. The digitized signal is applied to D/A convertor 68 which converts the digitized signal back to the analog reference signal defining a zero offset input voltage. When the zero offset input voltage is equal to the zero offset output voltage, the analog difference signal goes to zero. Counter 66 digitally encodes the initial amplitude of the analog difference signal as a count of the number of pulses in the fast clock signal developed by clock 70 and applied to input C occurring before the analog difference signal goes to zero.

Upon the occurrence of the trailing edge of the second pulse which terminates the zero calibration cycle, switch 78 closes to recouple summing junction 34 to each of the output of second comparator 64 and the inverting input of first comparator 62 for application of the zero offset input voltage to summing junction 34. Furthermore, the trailing edge of the delayed pulse applied to start count input SC of counter 66 disables the counter and the digitized signal is stored, the stored digitized signal being a digital equivalent of the zero offset input voltage.

Upon power up of amplifier means 28', means (not shown) develops a momentary reset pulse which is applied to the start count input SC of counter 66 and first switch 76. For the duration of the reset pulse, switch 76 couples the non-inverting input of first comparator 62 to ground. The source of reference potential $V_{ref}$ applied to the non-inverting input of second comparator 64 is selected to provide an output voltage of $-1$ volt for application to the inverting input of first comparator 62. Inasmuch as the analog difference signal is negative during the duration of the reset pulse, the digitized signal developed by clocking the analog difference signal into counter 66 during the duration of the reset pulse resets the digitized signal.

Amplifier means 28' in one embodiment of the present invention is particularly useful in the anesthetic agent analyzer hereinabove described. To provide good zero stability of amplifier means 28' in the agent analyzer, the zero calibration cycle may be initiated every 30 minutes and have a duration of 100 microseconds. Thus, the slow clock signal has a time period of 30 minutes and a pulse width of 100 microseconds. The second pulse developed by one shot multi-vibrator 72 in response to the slow clock signal may be further useful for activating solenoid valves (not shown) of sample cell 14 to wash out the gas mixture with zero air. The delay of time delay 74 is selected to apply the second pulse to input SC when wash out of cell 14 is complete. Upon the occurance of the trailing edge of the second pulse, the solenoid valves would be deactivated to wash in the gas mixture. The total time required for wash in-wash out determines the pulse width of the second pulse.

There has been described novel apparatus and techniques with respect to particular embodiments of a non-dispersive infrared gas analyzer. It will be appreciated at various alterations, modifications and adaptations will become apparent to those skilled in the art from the foregoing description and accompanying drawings. Such alterations, modifications and adaptations are intended to be within the spirit and scope of the present invention defined solely by the appended claims.

What is claimed is:

1. A non-dispersive gas analyzer comprising:
   a gas cell for containing a gas mixture to be analyzed, said mixture including a selected one of a plurality of gases, each of said gases having the characteristic of absorbing radiant energy within a particular range of wavelengths;
   means for directing pulse modulated radiant energy through said cell, the modulation being at a predetermined frequency;
   detector means responsive to said radiant energy at a preselected wavelength for developing an AC signal having an amplitude determined by said radiant energy passing through said cell and a frequency corresponding to said predetermined frequency, said preselected wavelength being within said particular range of wavelengths for each of said gases;

means responsive to said AC signal for developing a DC signal having an amplitude determined from said AC signal; and means for adjusting the amplitude of said DC signal in proportion to the relationship between the energy absorption of said selected one of said gases at said preselected wavelength and a reference amplitude to provide an adjusted DC signal proportional to the concentration of said selected one of said gases in said mixture.

2. A non-dispersive gas analyzer as set forth in claim 1 wherein said adjusting means includes:

amplifier means responsive to said DC signal for developing said adjusted DC signal; and variable feedback means responsive to each of said DC signals for providing a plurality of gain steps in said amplifier means, each of said gain steps being associated with a different one of said gases.

3. A non-dispersive gas analyzer as set forth in claim 2 wherein said variable feedback means includes:

a T circuit having a first conductive branch, a second conductive branch and a third conductive branch all coupled at a common node, said DC signal being resistively applied to said first branch, said adjusted DC signal being applied to said second branch, said third branch being coupled between said node and ground, said third branch having a plurality of parallel conductive paths and a switch, each of said conductive paths being associated with a different one of said gain steps, said switch selectively coupling one of said paths between said node and ground.

4. A non-dispersive gas analyzer as set forth in claim 3 wherein each of said conductive paths includes a resistance, each of said gain steps being determined by said resistance of each of said conductive paths associated therewith.

5. A non-dispersive gas analyzer as set forth in claim 3 wherein said first conductive path includes a variable resistor, said adjusted DC signal having a span determined by said variable resistor.

6. A non-dispersive gas analyzer in accordance with claim 2 wherein said amplifier means includes:

an amplifier having an input and an output;

a variable resistor coupled to said input, said DC signal being applied to each of said input and said feedback means through said variable resistor, said output developing said adjusted DC signal, said adjusted DC signal having a zero voltage level determined by said variable resistor in the absence of said gases in said mixture.

7. A non-dispersive gas analyzer set forth in claim 6 wherein said amplifier further includes:

a source of potential having an opposite polarity to the polarity of said input; and a resistance coupled between said source and said input, said variable resistor further determining a current applied to said input.

8. A non-dispersive gas analyzer set forth in claim 7 wherein said feedback means includes:

a T circuit having a first current branch, a second current branch and a third current branch all coupled at a common node, said first current branch coupled between said input and said node, said second current branch coupled between said output and said node, said third current branch coupled between said node and ground.

9. A non-dispersive gas analyzer in accordance with claim 1 wherein said preselected wavelength is 3.3 microns.

10. A non-dispersive gas analyzer comprising:

a gas cell for containing one of a first gas mixture and a second gas mixture, said first gas mixture including a selected one of a plurality of analyte gases to be analyzed, each of said analyte gases having the characteristic of absorbing radiant energy within a particular range of wavelengths, said second gas mixture including a surrogate gas having the characteristic of absorbing radiant energy at a preselected wavelength common to the particular range of absorption wavelengths of each of said analyte gases;

means for directing pulse modulated radiant energy through said cell, the modulation being at a preselected frequency;

detector means responsive to said radiant energy at said preselected wavelength for developing a first signal determined from said radiant energy passing through said cell at said preselected frequency;

means for adjusting said first signal to a second signal proportional to the concentration of a selected one of said analyte gases, said adjusting means including means for adjusting said first signal in proportion to the relationship between the radiant energy absorbed by said selected analyte gases at said preselected wavelength and the radiant energy at said preselected wavelength absorbed by said surrogate gas.

* * * * *